United States Patent [19]

Harris et al.

[11] Patent Number: 5,210,171
[45] Date of Patent: May 11, 1993

[54] PROCESS TO POLYMERIZE AB-PBO MONOMER PHOSPHATE SALTS

[75] Inventors: William J. Harris; Zenon Lysenko, both of Midland; Carl W. Hurtig, Saginaw, all of Mich.

[73] Assignee: The Dow Chemical Company, Midland, Mich.

[21] Appl. No.: 546,597

[22] Filed: Jun. 29, 1990

Related U.S. Application Data

[63] Continuation-in-part of Ser. No. 380,567, Jul. 14, 1989, Pat. No. 4,959,492.

[51] Int. Cl.$^5$ .................. C08G 63/00; C08G 63/02; C08G 79/02
[52] U.S. Cl. ............................ 528/168; 528/167; 528/176; 528/179; 528/183; 528/184; 528/206; 528/207
[58] Field of Search .............. 528/167, 168, 176, 179, 528/183, 184, 206, 207

[56] References Cited

U.S. PATENT DOCUMENTS 4,772,678  9/1988  Sybert .................. 528/179

FOREIGN PATENT DOCUMENTS 62-89760  10/1988  Japan .

OTHER PUBLICATIONS

Imai et al., "Polybenzazoles," 83 *Makromol. Chem.* 179 (1965).
Wolfe, "Polybenzothiazoles and Polybenzoxazoles," 11 *Encyclopedia Poly. Sci. & Tech.*, 601.

*Primary Examiner*—John Kight, III
*Assistant Examiner*—T. Mosley

[57] ABSTRACT

AB-polybenzoxazole monomer, such as 3-amino-4-hydroxybenzoic acid, can be synthesized in high yields from a hydroxy-benzoic acid or related compound in a three-step process of (1) nitration, (2) hydrolysis of the ester, and (3) reduction of the nitro moiety. The monomer is conveniently recovered as a phosphate salt in high purity by precipitating and recrystallizing from a phosphoric acid solution. The monomer may be polymerized in high concentrations in polyphosphoric acid containing high levels of $P_2O_5$ to yield a high molecular weight polymer without dehydrohalogenation.

13 Claims, No Drawings

PROCESS TO POLYMERIZE AB-PBO MONOMER PHOSPHATE SALTS

CROSS-REFERENCE TO RELATED APPLICATION

This application is a continuation-in-part of copending application Ser. No. 380,567, filed Jul. 14, 1989, now U.S. Pat. No. 4,959,492.

BACKGROUND OF THE INVENTION

The present invention relates to AB-polybenzoxazole (AB-PBO) monomers and processes for synthesizing and polymerizing them.

AB-polybenzoxazole monomers comprise:

(1) an aromatic group:

(2) an o-amino-hydroxy moiety bonded to said aromatic group, which consists of a primary amine group bonded to said aromatic group and a hydroxy group bonded to said aromatic group in a position ortho to said primary amine group; and (3) an electron-deficient carbon group linked to said aromatic group. AB-polybenzoxazole monomers preferably conform with formula I:

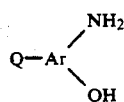

wherein Q is an electron-deficient carbon group: Ar is an aromatic group; and the amine and hydroxy groups are in ortho position with respect to each other.

The monomer is polymerized by polycondensation in a non-oxidizing solvent acid, such as methanesulfonic acid or polyphosphoric acid, at elevated temperatures, as described in Sybert et al., *Liquid Crystalline Polymer Compositions, Process and Products*, U.S. Pat. No. 4,772,678 (Sep. 20, 1988): Wolfe et al., *Liquid Crystalline Polymer Compositions, Process and Products*, U.S. Pat. No. 4,703,103 (Oct. 27, 1987); Wolfe et al., *Liquid Crystalline Polymer Compositions, Process and Products*, U.S. Pat. No. 4,533,692 (Aug. 6, 1985); Wolfe et al., *Liquid Crystalline Poly(2,6-Benzothiazole) Compositions, Process and Products*, U.S. Pat. No. 4,533,724 (Aug. 6, 1985); Wolfe, *Liquid Crystalline Polymer Compositions, Process and Products*, U.S. Pat. No. 4,533,693 (Aug. 6, 1985): Evers, *Thermoxidatively Stable Articulated p-Benzobisoxazole and p-Benzobisthiazole Polymers*, U.S. Pat. No. 4,359,567 (Nov. 16, 1982): Tsai et al., *Method for Making Heterooyclic Block Copolymer*, U.S. Pat. No. 4,578,432 (Mar. 25, 1986) and 11 Ency. Poly. Sci. & Eng., *Polybenzothiazoles and Polybenzoxazoles*, 601 (J. Wiley & Sons 1988), which are incorporated herein by reference.

The resulting polymers comprise a plurality of mer units which each contain:

(1) an aromatic group: and (2) an oxazole ring fused to said aromatic group and linked at the 2-carbon to an aromatic group in an adjacent mer unit. The polymers preferably comprise a moiety which conforms to formula II

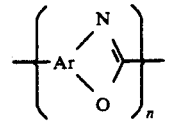

wherein n is a number of repeating units in excess of one.

The o-amino-hydroxy moiety of the AB-PBO monomer is extremely sensitive to air oxidation as a free base, so the monomer is ordinarily stored as an acid salt of hydrogen chloride. The release of hydrogen chloride gas during polymerization causes foaming of the polymerization mixture which can interfere with the reaction. Typically, the monomer is dehydrohalogenated at moderate temperatures and, optionally, reduced pressure, in a solution of polyphosphoric acid having low viscosity, and then phosphorus pentoxide is added to the solution before polymerizing to high molecular weight, as described in U.S. Pat. No. 4,533,693.

The known reaction sequences are inefficient for a number of reasons. Dehydrohalogenation is time consuming, and the low initial levels of phosphorus pentoxide slow the initial stages of the reaction even further. Moreover, the reactor must be made using materials which are suitable for contact with the hydrogen halide gas that is released by during the dehydrohalogenation step.

What is needed is a process for polymerizing AB-PBO monomer without dehydrohalogenation in high initial concentrations in a solvent acid of high initial viscosity.

SUMMARY OF THE INVENTION

The present invention is a process for synthesizing a polybenzazole polymer, said process comprising the steps of:

(1) mixing a phosphate salt of an AB-PBO monomer with a polyphosphoric acid containing at least 80 percent $P_2O_5$ by weight at the commencement of the reaction in a concentration of monomer to polyphosphoric acid that is chosen such that the solution resulting from polymerization contains at least 7 weight percent polymer and less than 30 weight percent polymer under non-oxidizing conditions: and (2) maintaining the mixture at a temperature and under conditions suitable to cause the AB-PBO monomer to form polymer for a period of time sufficient to form a polybenzazole polymer containing AB-PBO mer units.

The phosphate salt and process for using it are advantageous because the phosphate salt may be polymerized rapidly in high concentrations in a solvent acid that initially contains high levels of $P_2O_5$ without foaming or its associated problems. The resulting AB-PBO polymers may have high inherent viscosities, indicating high molecular weight

DETAILED DESCRIPTION OF THE INVENTION

Definitions

The following terms are used in this application and are defined here for convenience.

AA-Monomer - A monomer suitable for synthesizing polybenzazole polymers, comprising two electron-deficient carbon groups linked by a divalent organic moiety (DM) which is inert with respect to all reagents under polybenzazole polymerization conditions. The electron-deficient carbon groups have the definition and preferred embodiments given herein. The divalent organic moiety is preferably alkyl or an aromatic group, as herein defined, is more preferably an aromatic group, and is most preferably a six-membered aromatic group. Examples of suitable AA-monomers and references to their synthesis are provided in U.S. Pat. No. 4,533,693 at Columns 25-32, Tables 4-6 Preferred examples of AA-monomers include terephthalic acid, isophthalic acid, bis-(4-benzoic) acid and oxy-bis-(4-benzoic) acid) and acid halides thereof.

AB-Monomer—A monomer suitable for synthesizing polybenzazole polymers, comprising an aromatic group, an o-amino-basic moiety bonded to the aromatic group, and an electron-deficient carbon group bonded to the aromatic group. The aromatic group, the electron-deficient carbon group and the o-amino-basic moiety have the definitions and preferred embodiments given herein Examples of suitable AB-monomers and processes for their synthesis are provided in U.S. Pat. No. 4,533,693 at Columns 33-35, Tables 7-8. Preferred examples of AB-monomers include 3-amino-4-hydroxybenzoic acid, 3-hydroxy-4-aminobenzoic acid, 3-mercapto-4-aminobenzoio acid and the acid halides thereof. AB-monomers are frequently stored as salts of hydrogen chloride or phosphoric acid, because the free-base of the monomer is unstable and susceptible to air oxidation.

Aromatic group (Ar)—any aromatic ring or ring system which can be part of a PBZ polymer. Each aromatic group may individually be heterocyclic, but each is preferably carbocyclic and more preferably hydrocarbyl. If an aromatic group is heterocyclic, it is preferably a nitrogen-containing heterocycle.

Each aromatic group may comprise a single aromatic ring, a fused ring system, or an unfused ring system, containing two aromatic moieties linked by a bond or a divalent linking moiety which is inert with respect to PBZ polymerization reagents under PBZ polymerization conditions. If the aromatic group comprises a divalent linking moiety, that moiety preferably comprises an ether linking moiety, a thioether linking moiety, a sulfonyl linking moiety, an alkyl linking moiety, or a halogenated alkyl linking moiety or known equivalents. The divalent linking moiety preferably comprises no more than about 6 carbon atoms Aromatic groups preferably consist essentially of a single ring.

Size of the aromatic group is not critical as long as the aromatic group is not so big that it prevents further reactions of the moiety in which it is incorporated. Each aromatic group preferably independently comprises no more than about 18 carbon atoms, more preferably no more than about 12 carbon atoms and most preferably no more than about 6 carbon atoms, excluding any divalent linking group and any organic substituent on the aromatic group.

Each aromatic group may independently have substituents which are stable in solvent acid and which do not interfere with the polymerization of monomers for PBZ synthesis, such as halogen atoms, alkoxy moieties, aryloxy moieties or alkyl moieties. Substituents which comprise organic moieties preferably comprise no more than about 12 carbon atoms, more preferably no more than about 6 carbon atoms. Each aromatic group preferably has no substituents other than those specified hereinafter.

Azole ring—an oxazole, thiazole or imidazole ring. The carbon atom bonded to both the nitrogen atom and the oxygen, sulfur or second nitrogen atom is the 2-carbon, as depicted in formula III

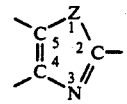

wherein Z is —O—, —S— or —NR—; and R is hydrogen, an aromatic group, an aliphatic group or an aliphatic-aromatic group, preferably hydrogen or an alkyl group, and most preferably hydrogen R preferably comprises no more than about 6 carbon atoms, more preferably no more than about 4 and most preferably no more than about 1. Each azole ring is independently preferably oxazole or thiazole and more preferably oxazole. In PBZ polymer, the 4 and 5 carbon atoms are ordinarily fused with an aromatic group.

Azole-forming moiety—an "o-amino-basic moiety" or "electron-deficient carbon group," as those terms are hereinafter defined.

o-Amino-basic moiety—a moiety bonded to an aromatic group, which o-amino-basic moiety contains
(1) a first primary amine group bonded to the aromatic group and
(2) a hydroxy, thiol or primary or secondary amine group bonded to the aromatic group ortho to said primary amine group. It preferably comprises a hydroxy, thio or primary amine moiety, more preferably comprises a hydroxy or thiol moiety, and most preferably comprises a hydroxy moiety. If the o-amino-basic moiety comprises two amine groups, preferably both are primary amine groups. If the o-amino-basic moiety contains a secondary amine group, the secondary amine group may comprise an aromatic or an aliphatic group but preferably comprises an alkyl group. The secondary amine group preferably comprises no more than about 6 carbon atoms, more preferably no more than about 4 carbon atoms and most preferably no more than about 1 carbon atom.

BB-Monomer—A monomer suitable for synthesizing polybenzazole polymers, comprising an aromatic group and two o-amino-basic moieties which are bonded to the aromatic group. The aromatic group and the o-amino-basic moieties have the definitions and preferred embodiments given herein. Examples of suitable BB-monomers and processes for synthesis are provided in U.S. Pat. No. 4,533,693 at Columns 19-24, Tables 1-3. Examples of preferred BB-monomers include 4,6-diaminoresorcinol, 2,5-diaminohydroquinone and 1,4-dithio-2,5-diaminobenzene. BB-monomers are frequently stored as salts of hydrogen chloride or phosphorio acid, because the free base of the monomer is susceptible to air oxidation.

Electron-deficient carbon group (Q)—any group containing a carbon atom which can react in the solvent acid with an o-amino-basic moiety to form an azole ring, such as the groups listed in Column 24, lines 59-66 of the U.S. Pat. No. 4,533,693, and such as an orthoester group, an amidate ester group, a trihalomethyl group or an alkali or alkaline-earth metal carboxylate group. Each electron-deficient carbon group is preferably independently a carboxylic acid or acid halide group and more preferably a carboxylic acid group. Halogens in electron-deficient carbon groups are preferably independently chlorine, bromine or fluorine and are more preferably chlorine.

Solvent acid—a non-oxidizing liquid acid capable of dissolving PBZ polymers, such as sulfuric acid, methanesulfonic acid, polyphosphoric acid and mixtures thereof. The solvent acid highly preferably either is a dehydrating acid or contains a dehydrating agent such as $P_2O_5$ Examples of preferred solvent acids include polyphosphoric acid and mixtures of methanesulfonic acid and phosphorus pentoxide. Polyphosphoric acid preferably has a $P_2O_5$ content by weight of at least about 70 percent, more preferably at least about 75 percent and preferably has a $P_2O_5$ content of at most about 90 percent, more preferably at most about 85 percent. The ratio of methanesulfonic acid to phosphorus pentoxide in mixtures of those compounds is preferably no more than about 20:1 by weight and no less than about 1:1 by weight. The most preferred solvent acid is polyphosphoric acid.

DESCRIPTION

AB-PBO monomer is preferably synthesized in a three-step process. The first step is the nitration of a hydroxy-ester compound, which contains:

(1) an aromatic group:
(2) a hydroxy group bonded to said aromatic group: and
(3) an ester group having a carboxylate ion linked to said aromatic group.

The aromatic group has the description and preferred embodiments previously given. The carboxylate ion may be linked to the aromatic group by an aliphatic moiety, but is preferably bonded directly to the aromatic group. The hydroxy moiety is preferably not ortho to the carboxylate ester. It is more preferably para to the carboxylate ester. Examples of suitable hydroxy-ester compounds include the methyl to hexyl esters of 4-hydroxybenzoate, 3-hydroxybenzoate, 4-(p-hydroxyphenyl)benzoate and 4-(p-hydroxyphenoxy)benzoate. The most preferred hydroxy-ester compound is a 4-hydroxybenzoate ester.

Some suitable hydroxy-ester compounds, such as methyl 4-hydroxybenzoate, are commercially available. Other suitable esters can be synthesized by known reactions such as esterification of an appropriate hydroxy-benzoic acid or transesterification of an appropriate hydroxy-benzoate ester. Suitable hydroxy-benzoic acids and related compounds can be synthesized by obvious variations of known syntheses, such as those described in B. S. Furniss, *Vogel's Practical Organic Chemistry* - 4th ed. 832 (Longman 1978): A. H. Blatt et al., 2 *Organic Syntheses* 343 (J. Wiley & Sons 1943): and Fieser, 58 *J. Am. Chem. Soc.* 1738 (1936).

The hydroxy-ester compound is contacted with a nitrating agent. The nitration of aromatic compounds is a well-known reaction. The conditions are familiar to persons of ordinary skill in the art, and are reported in numerous references, such as G. M. Loudon, *Organic Chemistry* 590, 598, 1283-86 (Addison-Wesley Publishing Co. 1984). The nitrating agent is preferably nitric acid. The nitric acid is preferably concentrated, such as about 70 to 71 percent nitric acid. The contact is made in a solvent capable of dissolving the hydroxy-ester compound. The solvent is preferably a halogenated aliphatic compound and is more preferably methylene chloride. The solvent must be inert with respect to nitration and with respect to all reagents under reaction conditions. The contact is made in the presence of a catalytic amount of strong acid, such as sulfuric acid. The temperature is preferably no more than about 25° C., more preferably no more than about 15° C. and most preferably no more than about 5° C. It is preferably no less than about −15° C., more preferably no less than about −10° C. and most preferably no less than about −5° C.

The nitration product comprises all of the elements of the hydroxy-ester compound, and further comprises a nitro group bonded to the aromatic group ortho to the hydroxy group. When the hydroxy group is para to the ester moiety, then the nitro groups are primarily all ortho to the hydroxy group. When the hydroxy group is in another position, the product may comprise a mixture of isomers which are separated by known techniques, such as recrystallization.

In the second step, the nitrated hydroxy-ester is converted to a water-soluble salt and dissolved in an aqueous solvent. The nitrated hydroxy-ester is preferably extracted into an aqueous solution by contact with an aqueous solvent and with a base which is in sufficient quantities and is selected such that the nitrated hydroxy-ester is converted into a nitrated hydroxy-benzoate salt which is soluble in water. The base is preferably an alkali or alkaline-earth metal hydroxide. The base is more preferably an alkali metal hydroxide, such as lithium, sodium or potassium hydroxide, and is most preferably sodium hydroxide. The base is preferably dissolved in the aqueous solvent The resulting water-soluble salt is preferably formed in yields of at least about 90 percent, more preferably at least about 95 percent and most preferably at least about 99 percent, based upon the initial amount of hydroxy-ester compound. The aqueous solution can be used for the third step without purification or isolation.

In the third step of the synthesis, the product from the second step is contacted with a hydrogenating agent in the presence of a catalytic amount of transition-metal catalyst in an aqueous solution under conditions such that the nitro group is hydrogenated and an AB-PBO monomer is formed. Reaction conditions for catalytic hydrogenation of nitro groups are well-known and are described in many standard texts, such as G. M. Loudon, *Organic Chemistry* 1197-98 (Addison-Wesley Publishing Co. 1984).

The contact occurs in an aqueous solution, which is preferably the solution produced in the extraction step. The hydrogenating agent is preferably molecular hydrogen. The catalyst is preferably contains nickel or a noble metal, such as platinum or palladium. It is more preferably a palladium catalyst. The catalyst is preferably supported and more preferably supported on carbon. Examples of suitable catalyst include 5 to 10 weight percent palladium-on-carbon. The reaction takes place in the presence of hydrogen. Of course, oxidizing gases such as oxygen must be excluded from the system. The temperature of the reaction is preferably at least about 30° C., more preferably at least about 20° C. and most preferably at least about 45° C. It is preferably at most about 110° C., more preferably at most about 95° C. and most preferably at most about 65° C.

The product of the hydrogenation step is an AB-PBO monomer in which the electron-deficient carbon group is a carboxylate salt. The positions of the amine, hydroxy and carboxylate groups in the monomer are determined by the position which they and their precursors held in the intermediates used to make the monomer. The monomer is dissolved in an aqueous solution, and is highly susceptible to air oxidation in its free-base state.

The AB-PBO monomer may be precipitated from the aqueous solution by contacting it with a non-oxidizing protic acid to convert the carboxylate salt moiety into a carboxylic acid moiety. The non-oxidizing protic acid is preferably chosen and in sufficient quantities to protonate the o-amino-hydroxy moiety of the monomer, in order to stabilize the monomer against air oxidation. The non-oxidizing protic acid is preferably a hydrogen halide or phosphoric acid, more preferably hydrochloric acid or phosphoric acid, and most preferably phosphoric acid. The monomer precipitates as an acid salt of the non-oxidizing protic acid. The monomer should not be exposed to air or other oxidizing media until it has been contacted with an acid to protonate the o-amino-hydroxy moiety.

The precipitated AB-PBO monomer phosphate salt can be purified by recrystallization from an aqueous phosphorio acid solution. The solution may contain a small amount of reducing agent, such as tin (II) chloride, to reduce any oxidized impurities in the monomer. The solution is heated to any temperature sufficient to cause essentially all of the monomer phosphate salt to dissolve The temperature is preferably at least about 80° C., more preferably at least about 90° C. and most preferably greater than 100° C. The solution is then cooled to a temperature sufficient to precipitate a substantial portion of monomer phosphate. The temperature is preferably at most about 10° C., more preferably at most about 5° C. and most preferably at most about 0° C.

The recrystallized monomer is preferably washed with a volatile organic non-solvent which forms an azeotrope with water. The non-solvent is preferably an alcohol having from 1 to 6 carbon atoms, and is more preferably ethanol. The monomer is preferably dried to remove essentially all water and free phosphoric acid.

The processes described above preferably produce at least about 75 percent yield of AB-PBO monomer based upon the beginning hydroxy-ester compound, and more preferably produce at least about 80 percent yield. The purity of AB-PBO monomer phosphate salt, as a weight percentage of the organic content which is AB-PBO monomer ion, is preferably at least about 99 percent, more preferably at least about 99.5 percent and most preferably at least about 99.9 percent by weight.

The AB-PBO monomer phosphate salt comprises ions of AB-PBO monomer and phosphoric acid. The AB-PBO monomer has the description previously given. The aromatic group has the description and preferred embodiments of the aromatic group in the initial hydroxy-ester compound. The electron-deficient carbon group has the meaning and preferred embodiments previously given. It is most preferably carboxylic acid. The electron-deficient carbon group is preferably para to the amine moiety or the hydroxy moiety, and most preferably to the hydroxy moiety. The AB-PBO monomer ion is most preferably an ion of 3-amino-4-hydroxybenzoic acid.

The phosphate ion may, in some cases, be a condensed phosphate, such as pyrophosphate, but is preferably a single phosphate. A single phosphate ion may have two or three AB-PBO monomer ions associated with it, but the average number of phosphate ions associated with each AB-PBO ion is preferably about 1:1.

AB-PBO monomer phosphate ions of the present invention may be polymerized in non-oxidizing solvent acid according to known processes. The solvent acid is preferably polyphosphoric acid. AB-PBO monomer phosphate salts may be polymerized in polyphosphoric acid that initially contains low levels of $P_2O_5$, such as about 77 weight percent, but they are preferably polymerized in polyphosphoric acid containing at least 80 percent $P_2O_5$ at the commencement of the reaction. The higher concentration of $P_2O_5$ speeds the reaction. Of course, the concentration of $P_2O_5$ drops as the reaction progresses, unless more $P_2O_5$ is added during the reaction. The initial concentration of $P2O5$ is more preferably at least 82 percent. The maximum concentration of $P_2O_5$ is limited primarily by practical concerns. At too high a concentration, the acid is too viscous to effectively wet the monomer.

AB-PBO monomer phosphate salts may be polymerized in low concentrations, such as 5 percent monomer or less, but they are advantageously polymerized in concentrations suitable to provide a liquid crystalline solution. The concentration of monomer in the solvent is preferably sufficient to provide a dope containing at least 7 weight percent polymer, more preferably at least 10 weight percent polymer, and most preferably at least 14 weight percent polymer. If the concentration of monomer is too high initially, then the mixture may not contain sufficient acid to wet the polymer. The concentration of monomer should be low enough to provide a dope containing less than 30 weight percent polymer, preferably no more than 20 weight percent polymer, and more preferably no more than 16 weight percent polymer.

The actual monomer concentrations necessary to obtain dopes having those concentrations vary, depending upon the monomer in question and upon whether all of the solvent is added initially or some polyphosphoric acid or phosphorus pentoxide is added after commencement of the reaction. Proper initial monomer concentrations can be calculated by persons of ordinary skill in the art. When 3-amino-4-hydroxybenzoic acid monophosphate and/or 4-amino-3-hydroxybenzoic acid monophosphate are polymerized, the concentration of AB-PBO monomer phosphate salt in the polymerization mixture (expressed as a weight percentage based upon the total weight of monomer salt, initial solvent acid, and any solvent acid or $P_2O_5$ added during the reaction) is preferably at least 15 percent, more preferably at least 21.5 percent, and most preferably at least 30 percent. The concentration is preferably less than 70 percent, more preferably at most 43 percent, and most preferably at most 36.5 percent. If the monomer is mixed in an initial polyphosphoric acid solution and more acid or $P_2O_5$ is added later, the initial concentration may be even higher than that preferred above, such as 50 percent or more.

The monomers in the solution may all be AB-PBO monomers. Such solutions polymerize to provide a dope containing AB-PBO homopolymer. Alternatively, the AB-PBO monomers may be copolymerized with other AB-monomers, such as salts of diamino-benzoic acid or amino-thiobenzoic acid: or with AA-and BB-monomers, such as terephthalic acid and 4,6-diaminoresorcinol or 2,5-diamino-1,4-dithiobenzene; or with segments of polybenzazole polymer that are terminated by a functional moiety. The polymers resulting from such a copolymerization are random, sequential or block copolymers which reflect to monomer mixture in the polyphosphoric acid at the time of the reaction. The reaction mixture may also contain monofunctional reagents, such as benzoic acid, to serve as chain terminators and limit molecular weight growth in the polymer, as described in U.S. Pat. No. 4,703,103, which is incorporated herein by reference.

The monomer may be mixed with the solvent acid by known means. When the electron-deficient carbon group does not contain halogen, no dehydrohalogenation step is necessary. Examples of suitable conditions for polymerization are discussed in U.S. Pat. Nos. 4,772,678; 4,703,103; 4,533,692; 4,533,724; 4,533,693; 4,359,567; and 4,578,432 and in 11 Ency. Poly. Sci. & Eng., supra. 601 and Ledbetter, "An Integrated Process for Preparing Rigid Rod Fibers from the Monomers," *The Materials Science and Engineering of Rigid Rod Polymers* 253 (1989), which are incorporated herein by reference. The maximum temperature during the reaction is preferably at least about 70° C., more preferably at least about 100° C., more highly preferably at least about 150° C. and most preferably at least about 190° C. The maximum temperature must be less than the decomposition point of reagents and products, and is preferably at most about 230° C., more preferably at most about 220° C. The reaction should be carried out under a non-oxidizing atmosphere, such as nitrogen, argon or vacuum, and with vigorous agitation. Agitation may be provided by known mechanisms, such as mechanical stirrers, press mixers or single- or multiple-screw extruders. Other conditions may be found in other literature references.

Under preferred conditions, the reaction proceeds very quickly to high viscosity. Stir opalescence may occur in as quickly as four hours using a conventional mechanical stirrer, and the dope may become too thick to stir thereafter. The reaction temperatures may be continued after the dope is too thick to stir, but it is theorized that little advancement in molecular weight occurs thereafter.

AB-PBO polymer produced by this process preferably has a molecular weight corresponding to an inherent viscosity in methanesulfonic acid at 25° C. and about 0.05 g/dL of at least 7 dL/g, more preferably at least 10 dL/g, more highly preferably at least 20 dL/g and most preferably at least 25 dL/g. The relationship between intrinsic viscosity and molecular weight for copolymers of AB-PBO varies depending upon the particular copolymer.

AB-PBO polymers and copolymers can be extruded into fibers and films useful for making composites and laminates according to the processes described in 11 Ency. Poly. Sci. & Eng., supra. at 625-31, which is incorporated herein by reference.

WORKING EXAMPLES

The following examples are for illustrative purposes only and are not intended to limit the scope of either the specification or the claims. All parts and percentages are by weight unless otherwise stated.

Example 1—Synthesis and Precipitation of AB-PBO Monomer Phosphate Salt

A 152.0-g (1.0 mole) quantity of methyl 4-hydroxybenzoate is dissolved in one liter of dichloromethane. The solution is cooled to 0° C. and 100 ml of 98 percent sulfuric acid is added. With vigorous stirring 80 ml of 71 percent nitric acid is added dropwise such that the temperature of the mixture did not exceed 5° C. The mixture is stirred an additional hour at 5° C. The mixture is diluted with 150 ml of water and the aqueous phase is separated.

The organic phase is diluted with 500 ml of dichloromethane, washed with 200 ml of water, and extracted with three 500-ml portions of aqueous sodium hydroxide containing 45 g (1.1 moles) of sodium hydroxide. The three aqueous extracts, containing sodium 4-hydroxy-3-nitrobenzoate are combined.

A 500-ml portion of the extract containing approximately 0.33 mole of sodium 4-hydroxy-3-nitrobenzoate is sealed in a one-liter Hastelloy C autoclave with 5.0 g of 5 percent palladium-on-carbon. The reactor is purged with nitrogen and charged to 400 psig with hydrogen gas. The reactor is heated to 45° C. and maintained at 300 psig to 400 psig hydrogen pressure until hydrogen uptake is completed. The reactor is purged with nitrogen, the catalyst is filtered and the solution is acidified with 600 ml of 85 percent phosphoric acid. The solution is cooled to 0° C. and crude 3-amino-4-hydroxybenzoic acid hydrophosphate salt is filtered.

The crude salt is added to a mixture of 600 ml of 85 percent phosphoric acid, 1.0 g of $SnCl_2 2H_2O$ dissolved in 50 ml of 35 percent HCl, and 100 ml of water. The slurry is heated to 150° C. and water is added in sufficient quantity to dissolve all solid material. A 5-g quantity of activated carbon is added and the solution is maintained at 150° C. for 10 minutes. The carbon is filtered, and the filtrate is cooled to 0° C. The resulting crystals are filtered, washed in cold n-propanol and dried under nitrogen gas. The recovered product contains 71 g (80 percent yield) of 3-amino-4-hydroxybenzoic acid hydrophosphate salt having one water of hydration.

Example 2—Synthesis of AB-PBO Phosphate Monomer with Nickel Reduction

The process of Example 1 is repeated, except that the reduction is carried out using 2.5 g of nickel catalyst at a temperature of 95° C. The yield is approximately the same.

Example 3—Polymerization of AB-PBO Monomer Phosphate Salt

Under nitrogen atmosphere, 15.00 g of 3-amino-4-hydroxybenzoic acid monophosphate is mixed with 13.8 g of polyphosphoric acid containing 83.9 percent $P_2O_5$. The mixture is heated with mechanical stirring under nitrogen atmosphere for 90 minutes at 95° C. The temperature is raised to 190° C. over a period of about 1 hour, with an additional 15.4 g of $P_2O_5$ added during this period. After another 2 hours the mixture became stir opalescent, and quickly thereafter it became too viscous to stir. Heating is continued until a total of 48 hours at 190° C. is reached. The dope is cut up, coagulated with water, extracted overnight with a Soxhlet extractor with water, dried in a vacuum oven, ground, extracted with water and redried in a vacuum oven. The resulting polymer had a formula as illustrated in Formula II wherein Ar is a 1,3,4 phenylene ring and the oxygen atom is bonded to the phenylene ring para to the tond linking that ring to other mer units. The inherent viscosity of the polymer is measured at a temperature of about 25° C. and a concentration of about 0.05 g/dL in methanesulfonic acid to be about 27.2 dL/g.

Example 4—Polymerization of AB-PBO Monomer Phosphate Salt

The process of Example 3 is repeated using 15.00 g of 3-amino-4-hydroxybenzoic acid monophosphate, 9 1 g of polyphosphoric acid, and 20.1 g of $P_2O_5$. The inherent viscosity of the polymer is measured at a temperature of about 25° C. and a concentration of about 0.05 g/dL in methanesulfonic acid to be about 24.0 dL/g.

Example A—Polymerization of AB-PBO Monomer Phosphate Salt

Under nitrogen atmosphere, 15.0 g of AB-PBO monomer phosphate salt from Example 1 and 6.43 g of polyphosphoric acid containing 77 weight percent $P_2O_5$ are agitated at 95° C. for 1.3 hours. No foaming is observed. A 17.6-g quantity of $P_2O_5$ is added, and agitation at 95° C. is continued for 4 hours. A 4.37-g quantity of polyphosphoric acid is added, and stirring is continued at 95° C. for 18 hours. The pressure is reduced to 160 mmHg, and stirring at 95° C. is continued for 24 hours. The temperature is raised to 190° C. with stirring at 160 mmHg for 24 hours.

The resulting dope is extruded according to known methods to form a fiber. AB-PBO polymer is coagulated from a sample of dope, washed with water, dried, ground, rewashed and redried. The polymer has an inherent viscosity of 14.5 dL/g in methanesulfonic acid at 25° C. and 0.0528 g/dL concentration.

What is claimed is:

1. A process for synthesizing a polybenzazole polymer without a dehydrohalogenation step said process comprising the steps of:
   (1) mixing a phosphate salt of an AB-PBO monomer with a polyphosphoric acid containing at least 80 percent $P_2O_5$ by weight at the commencement of the reaction in a concentration of monomer to polyphosphoric acid that is chosen such that the solution resulting from polymerization contains at least 7 weight percent polymer and less than 30 weight percent polymer under non-oxidizing conditions to form a polymerization mixture: and
   (2) maintaining the polymerization mixture at a temperature and under conditions suitable to cause the AB-PBO monomer to form polymer for a period of time sufficient to form a polybenzazole polymer containing AB-PBO mer units.

2. The process of claim 1 wherein step 2 is carried out at a temperature between about 60° C. and about 230° C. under a non-oxidizing atmosphere or vacuum with agitation.

3. The process of claim 2 wherein the AB-PBO monomer contains: (1) a carbocyclic aromatic group having no more than about 18 carbon atoms, (2) an o-aminobasic moiety consisting of a primary amine group and a hydroxy group bonded to the aromatic group in ortho positions with respect to each other, and (3) an electron-deficient carbon group bonded to the aromatic group in a position not ortho to either member of the o-aminobasic moiety.

4. The process of claim 3 wherein the aromatic group of the AB-PBO monomer is a 1,3,4-phenylene group.

5. The process of claim 4 wherein the AB-PBO monomer is 3-amino-4-hydroxybenzoic acid.

6. The process of claim 4 wherein the AB-PBO monomer is 3-hydroxy-4-aminobenzoic acid.

7. The process of claim 4 wherein the concentration of AB-PBO monomer phosphate salt in the polymerization mixture (expressed as a weight percentage based upon the total weight of monomer salt, initial solvent acid, and any solvent acid or $P_2O_5$ added during the reaction) is between about 15 percent and 70 percent.

8. The process of claim 4 wherein the concentration of AB-PBO monomer phosphate salt in the polymerization mixture (expressed as a weight percentage based upon the total weight of monomer salt, initial solvent acid, and any solvent acid or $P_2O_5$ added during the reaction) is between about 21.5 percent and 43 percent.

9. The process of claim 4 wherein the concentration of AB-PBO monomer phosphate salt in the polymerization mixture (expressed as a weight percentage based upon the total weight of monomer salt, initial solvent acid, and any solvent acid or $P_2O_5$ added during the reaction) is between about 30 percent and 36.5 percent.

10. The process of claim 7 wherein the monomers in the polymerization mixture are essentially all AB-PBO monomers, and the resulting polymer is an AB-PBO homopolymer.

11. The process of claim 10 wherein the AB-PBO polymer has an inherent viscosity of 10 dL/g or more in methanesulfonic acid at a concentration of about 0.05 g/dL and a temperature of about 25° C.

12. The process of claim 7 wherein the polymerization mixture further contains AA-monomers and BB-monomers, such that a random or sequential copolymer is formed.

13. The process of claim 7 wherein the polymerization mixture further contains a PBZ polymer or oligomer having a functional end group, such that a block copolymer is formed.

* * * * *

UNITED STATES PATENT AND TRADEMARK OFFICE
CERTIFICATE OF CORRECTION

PATENT NO. : 5,210,171
DATED : May 11, 1993
INVENTOR(S) : W. J. Harris, C. W. Hurtig, & Z. Lysenko It is certified that error appears in the above-indentified patent and that said Letters Patent is hereby corrected as shown below:

Column 1, line 11,   please insert
--STATEMENT OF GOVERNMENT INTEREST
    This invention was made with government support under Contract F33615-85-C-5113 awarded by the Department of the Air Force. The government has certain rights in this invention.--

Signed and Sealed this

Twenty-second Day of July, 1997

*Attest:*

BRUCE LEHMAN

*Attesting Officer*                *Commissioner of Patents and Trademarks*